US008684996B2

(12) United States Patent
Haueter et al.

(10) Patent No.: US 8,684,996 B2
(45) Date of Patent: Apr. 1, 2014

(54) METHOD AND APPARATUS FOR SETTING A BASAL RATE PROFILE FOR AN INSULIN PUMP

(75) Inventors: Ulrich Haueter, Grosshochstetten (CH); Daniel Von Buren, Sierentz (FR); Catalin Cris, Wunnewil (CH); Stephan Marcin, Kirchberg (CH)

(73) Assignee: Roche Diagnostics International AG, Rotkreuz (CH)

( * ) Notice: Subject to any disclaimer, the term of this patent is extended or adjusted under 35 U.S.C. 154(b) by 83 days.

(21) Appl. No.: 13/038,635

(22) Filed: Mar. 2, 2011

(65) Prior Publication Data

US 2012/0059348 A1    Mar. 8, 2012

Related U.S. Application Data

(63) Continuation of application No. PCT/EP2009/005448, filed on Jul. 28, 2009.

(30) Foreign Application Priority Data

Sep. 2, 2008  (EP) ................................. 08015448

(51) Int. Cl.
  *A61M 31/00*  (2006.01)
  *A61K 9/22*  (2006.01)
  *A61M 37/00*  (2006.01)
(52) U.S. Cl.
  USPC .................... 604/500; 604/890.1; 604/892.1; 604/131
(58) Field of Classification Search
  USPC ............ 604/500, 890.1, 892.1, 131; 715/700; 700/282
  See application file for complete search history.

(56) References Cited

U.S. PATENT DOCUMENTS

| | | | |
|---|---|---|---|
| 6,668,196 B1 * | 12/2003 | Villegas et al. | 607/60 |
| 2003/0163789 A1 * | 8/2003 | Blomquist | 715/526 |
| 2004/0055611 A1 | 3/2004 | Penny et al. | |
| 2005/0171513 A1 * | 8/2005 | Mann et al. | 604/890.1 |
| 2005/0272640 A1 | 12/2005 | Doyle, III et al. | |
| 2006/0132460 A1 * | 6/2006 | Kolmykov-Zotov et al. | 345/173 |
| 2007/0106135 A1 * | 5/2007 | Sloan et al. | 600/322 |
| 2007/0112298 A1 * | 5/2007 | Mueller et al. | 604/65 |
| 2007/0124002 A1 * | 5/2007 | Estes et al. | 700/20 |
| 2008/0306444 A1 * | 12/2008 | Brister et al. | 604/131 |
| 2009/0055149 A1 * | 2/2009 | Hayter et al. | 703/11 |
| 2010/0064243 A1 * | 3/2010 | Buck et al. | 715/773 |

FOREIGN PATENT DOCUMENTS

EP    1983456 A1    10/2008

OTHER PUBLICATIONS

Lamb et al., MR Imaging of Regional Cardiac Function: Low-Pass Filtering of Wall Thickness Curves, MRM, vol. 34, pp. 498-502, 1995.*
International Search Report, Appl. No. PCT/EP2008/005448, 3 pages, Oct. 26, 2009.

* cited by examiner

*Primary Examiner* — Bhisma Mehta
*Assistant Examiner* — Lauren M Peng
(74) *Attorney, Agent, or Firm* — Dinsmore & Shohl LLP

(57) ABSTRACT

Methods for setting a basal rate profile for an insulin pump, wherein the basal rate profile defines a basal rate delivery for a selected time interval and has a pre-defined number of profile segments each of which define the basal rate delivery for a subset of the selected time interval, include providing a curve representing the basal rate as a continuous function of time as an input for an input unit and generating the basal rate profile from the curve by a calculation unit by assigning curve values at selected time instances to the pre-defined number of profile segments.

20 Claims, 2 Drawing Sheets cursor starting point/end point of the curve adjacent profile segments with small deviation in height adjacent profile segments with large deviation in height

METHOD AND APPARATUS FOR SETTING A BASAL RATE PROFILE FOR AN INSULIN PUMP

CROSS REFERENCE TO RELATED APPLICATIONS

This application is a continuation of International Application No. PCT/EP2009/005448 filed Jul. 28, 2009 which claims priority to European Patent Application No. EP 08015448.7 filed on Sep. 2, 2008, both of which are incorporated by reference herein.

TECHNICAL FIELD

The present specification relates to methods and apparatuses for setting basal rate profiles for an insulin pumps.

BACKGROUND

A basal rate profile defines basal rate delivery for a selected time interval. It can have a pre-defined number of profile segments each defining the basal rate delivery for a subset of the selected time interval (i.e., a so-called time interval subset). The basal rate profile may also be defined by a steady mathematical function. In this case, each profile segment can correspond to a specific value of the mathematical function. The time interval subsets can then correspond to the time instances associated with the values of the mathematical function. Hence, the expression "profile segment" can also refer to a single value of a basal rate profile and the expression "time interval subset" or "subset of the selected time interval" can also refer to a single time instance of the selected time interval.

A basal rate profile for an insulin pump can comprise basal rate values for 24 hours, i.e. basal rate values for an entire day. In the case of diabetes, the basal rate defines a low rate of continuous insulin supply/delivery needed for controlling cellular glucose and amino acid uptake. The basal rate can be given in the unit IU/h (international unit per hour). The expression "basal rate profile" according to the present specification is also used for a part/time segment of another basal rate profile, e.g. of a 24-hour basal rate profile, that is stored in an insulin pump.

However, programming and changing of basal rates can require the manipulation of all profile segments of a stored basal rate profile. For example, if the selected time interval is 24 hours and the subset of the selected time interval is 1 hour, then there are 24 profile segments. If the subset of the selected time interval is 30 minutes, then there are 48 profile segments. Having to manipulate all profile segments thus might lead to high programming effort that can be reduced by defining less profile segments which, however, might lead to simpler, blockier basal rate profiles and decreased preciseness of medical treatment. Furthermore, the start basal rate and the end basal rate of a 24-hour basal rate profile may not be adjusted such, that an immediate repetition of the same basal rate profile, for example at midnight, might entail an unintentional jump in the basal rate delivery.

In some methods for setting basal rates for an implantable insulin pump, the delivery rates need not be entered for each subset of the selected interval of time, but only for those subsets that represent a change in delivery rate compared to a previous subset. In these methods, the selected time interval can be 24 hours beginning at midnight and the subset of the selected time interval can be 30 minutes. Hence, each set of basal rates would consist of 48 rates that can start on any half-hour of the day.

With some computer software (e.g., "ACCU-CHEK Insulin Pump Configuration Software Pro"), a 24-hour basal rate profile with 24 profile segments can be set by either inputting all 24 basal rate values required for the 24 profile segments into the personal computer via a keyboard and typing in the values, or by pressing scroll buttons with respect to the values for all profile segments, or even by pressing a mouse button, moving the mouse (thereby moving a cursor) and then releasing the mouse button, thereby increasing or decreasing bars with a cursor such that each bar represents a profile segment. The personal computer on which the software is installed can be connected to an insulin pump.

Furthermore, a basal rate profile can be set by defining a number of supporting points for the basal rate profile via an input unit of an insulin pump, generating a continuous function in accordance with the supporting points by means of a calculation unit of the insulin pump, and generating a time sequence of basal rates from the continuous function by the calculation unit.

Therefore, a need exists for alternative methods and apparatuses for setting a basal rate profile for an insulin pump

SUMMARY

In one embodiment, a method is provided for setting a basal rate profile for an insulin pump. The basal rate profile defines a basal rate delivery for a selected time interval and has a pre-defined number of profile segments each of which define the basal rate delivery for a subset of the selected time interval. The method includes providing a curve representing the basal rate as a continuous function of time as an input for an input unit and generating the basal rate profile from the curve by a calculation unit by assigning curve values at selected time instances to the pre-defined number of profile segments.

In another embodiment, an apparatus that sets a basal rate profile is provided. The basal rate profile defines a basal rate delivery for a selected time interval and has a pre-defined number of profile segments each of which define the basal rate delivery for a subset of the selected time interval. The apparatus includes an input unit that receives an input of a curve representing the basal rate as a continuous function of time and a calculation unit that generates the basal rate profile from the curve by assigning curve values at selected time instances to the pre-defined number of profile segments.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed desertion of the illustrative embodiments can be understood when read in conjunction with the following drawings where like structure is indicated with like reference numerals and in which:

DETAILED DESCRIPTION

As will become appreciated herein, methods and apparatuses are provided for setting a basal rate profile which is user-friendly, requires little effort and is easy to implement. Methods and an apparatuses are also provided for which setting/programming of a physiologically inappropriate basal rate profile can be avoided; i.e. the methods and the apparatuses disclosed herein are robust/safe with respect to potential physiologically inappropriate basal rate profiles.

Figure 1:
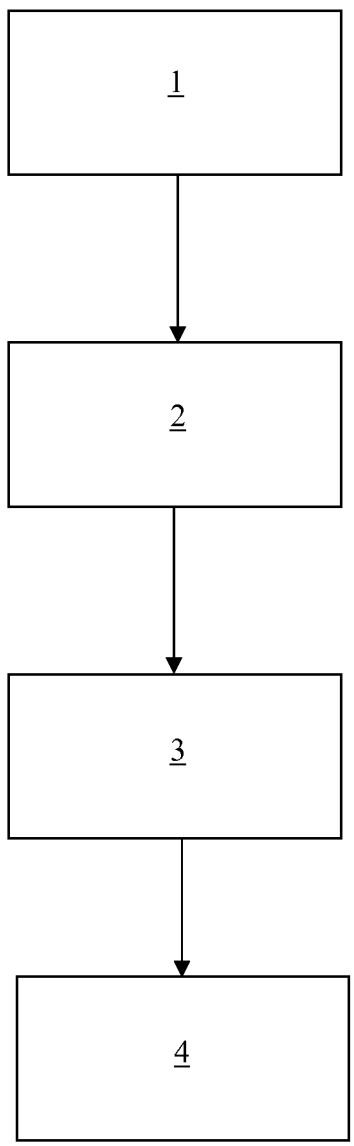
FIG. 1 depicts a flowchart of the method according to one or more embodiments shown and described herein.

Referring now to FIG. 1, a flowchart of a method for setting a basal rate profile is illustrated. In step 1, a curve representing a basal rate can be provided as a continuous function as an input for an input unit, such as, for example, by scanning a drawn curve, or by drawing a curve by hand on a display area of a touch screen or by means of a mouse on a display area of a personal computer, respectively. In step 2, this curve can optionally be smoothed by filtering. In step 3, each profile segment of the basal rate profile to be generated can be assigned a value of the curve, thereby generating the basal rate profile. In some embodiments, the time instance of the respective curve value corresponds to the middle time instance of the time interval subset of the respective profile segment. The deviation between curve values assigned to adjacent profile segments can be monitored and the curve values can be corrected if the deviation exceeds a pre-defined threshold. In some embodiments, in optional step 4, the generated basal rate profile can be further manipulated such as, for example, by scaling in the time domain, shifting in the time domain, multiplication with a specific factor, adding/subtracting a specific constant, while, for example, the basal delivery volume and/or its mean value is kept constant, if applicable. In some particular embodiments, the manipulation can be performed by subtracting the mean value of the provided curve, scaling the intermediate curve resulting from the subtraction (which has a mean value of zero) with a specific factor, and adding to this (further) intermediate curve resulting from the scaling the mean value.

Figure 2:
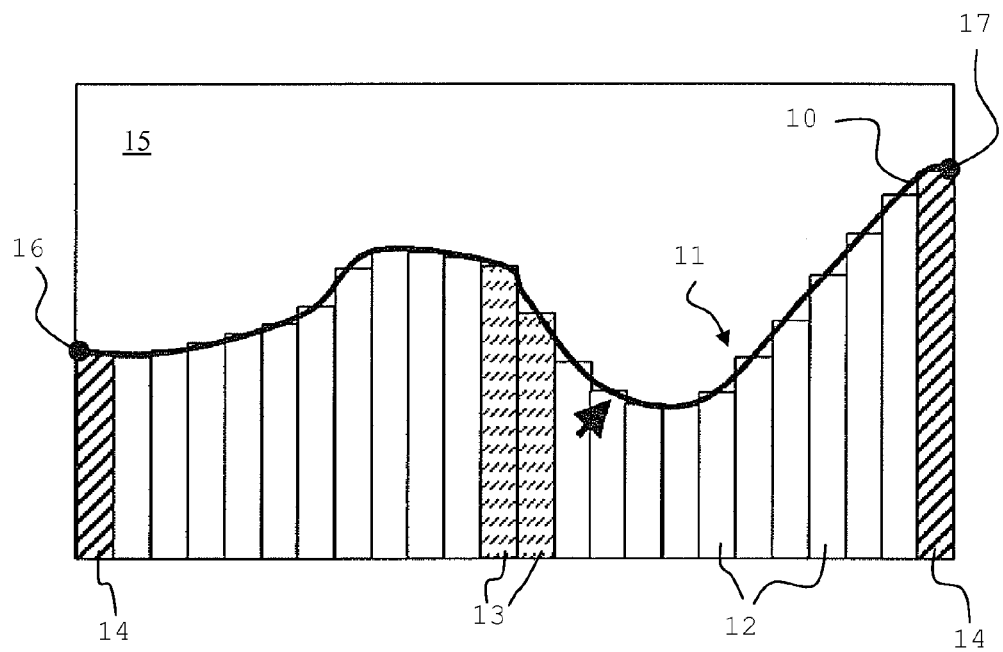
FIG. 2 depicts a display area with a graph illustrating a provided curve representing basal rates and a basal rate profile generated by the method according to one or more embodiments shown and described herein.
Figure 2:
Figure 2:
Figure 2:
Figure 2:

Referring now to FIG. 2, a display area 15 is illustrated with a graph illustrating a provided curve 10 representing basal rates and a basal rate profile 11 generated by the methods disclosed herein. As illustrated, the basal rate profile 11 consists of 24 profile segments 12, 13, 14 and defines basal rate delivery exemplarily for 24 hours. Each profile segment 12, 13, 14 defines the basal rate delivery exemplarily for 1 hour. The time may be provided on the X-axis, such as in hours, and the basal rate may be provided on the Y-axis, such as in IU/h. The profile segments may have varying time durations, i.e. they may be associated with different subsets of the selected overall time interval.

By moving an input unit such as a pointing device, for example the cursor (with its mouse button being pressed or, alternatively, after first selecting a clearly marked so-called action button or the like) or by moving a finger on a touch screen, the curve 10 can be drawn on the display area 15. The starting time/starting point 16 of the curve 10 can be defined by the first pressing of the mouse button or the first contact of the finger on the touch screen, respectively. The end time/end point 17 of the curve 10 can similarly be defined by releasing the mouse button or by removing the finger from the touch screen, respectively. Some adjacent profile segments, (e.g., profile segments 12 and 13) can have a small deviation in height which does not exceed the pre-defined threshold and which therefore results in physiological basal rate delivery.

The profile segments 14 can also be considered as adjacent profile segments as they are the first profile segment and the last profile segment in time and the generated basal rate profile is aimed for repetition without interruption. Such profile segments 14 can have a large deviation in height that exceeds the pre-defined threshold and thus be considered to be non-physiological. The heights of the profile segments 14 can therefore be corrected such that their deviation does not exceed the pre-defined threshold.

These methods and apparatuses can be further appreciated in light of the following exemplary embodiments. For example, in some embodiments, the method for setting a basal rate profile for an insulin pump comprises providing a curve that represents the basal rate as a continuous function of time as an input for an input unit and generating a basal rate profile from the curve by a calculation unit by assigning curve values at selected time instances to the number of profile segments of the basal rate profile. In some embodiments, the basal rate profile is defined as a mathematical function of the curve and values at selected time instances are assigned by the calculation unit to corresponding values of the mathematical function, such as at the same time instances. In such embodiments, the insulin pump can control basal rate delivery according to the mathematical function. In even some embodiments, the mathematical function is an approximation of the provided curve which represents the basal rate.

Further, in some embodiments, an apparatus for setting a basal rate profile according to the methods described herein comprises an input unit for inputting a curve representing the basal rate as a continuous function of time, and a calculation unit for generating the basal rate profile from the curve by assigning curve values at selected time instances to the number of profile segments.

The basal rate profile can define a basal rate delivery for a 24-hour day as the selected time interval. The curve values, i.e. the amplitude values of the provided curve with respect to the abscissa, constitute the basal delivery profile and the entire basal delivery volume is given by the integral of the curve over the selected time interval, or in particular, over 24 hours, i.e. an entire day. The subset of the selected time interval for each profile segment may comprise 1 hour such that it results in 24 profile segments. In other embodiments, the subset may comprise 30 minutes such that it results in 48 profile segments, or may comprise 2 hours such that it results in 12 profile segments. The choice of time interval subset for the profile segments may depend on the precision and/or the resolution of the employed insulin pump. Furthermore, in some embodiments, the respective time interval subset may vary for each profile segment and in particular depend on the dynamics of the curve, i.e. its amplitude/absolute value variation.

The basal rate profile (and hence the curve) may also represent part of a 24-hour profile or another basal rate profile that is stored in the insulin pump and that is longer in time. The basal rate profile may also only comprise one profile segment, such that by setting a one-profile-segment basal rate profile, only one profile segment of a longer basal rate profile that is already stored in the insulin pump is changed.

In some embodiments, an insulin pump can perform basal delivery in a pulsed way with insulin pulses being delivered with a given time interval of, for example, 3 minutes. In such embodiments, the number of profile segments may also be such that each profile segment defines the delivery with respect to one insulin pulse. For a time interval of 3 minutes, for example, this leads to 20 profile segments per hour.

In some embodiments, the calculation unit forms part of the insulin pump. Furthermore, in some embodiments, the input unit may form part of the insulin pump. However, the input unit and/or the calculation unit may also be provided by a separate device, i.e. by a device separate and/or remote from the insulin pump such as, for example, a dedicated remote controller, a personal digital assistant (PDA), or a personal computer (PC). Furthermore, the calculation unit can be provided by a separate device and be integrated into the device such as a PDA or a PC. The input unit and the calculation unit may form part of the same device that is separate from the insulin pump, or may form part of separate devices that are each separate from the insulin pump.

In some embodiments, the curve is manually provided. The curve may optionally be displayed on a display area of the input device while or after it is provided. The input device may also be provided by or comprise a touch screen with a display area. In such embodiments, the curve may be provided by continuously moving an object, such as a human finger or a stylus, across the display area. The touch screen may form part of the insulin pump or it may form part of a separate device such as a PDA or PC. In some embodiments, the curve is drawn in one go (e.g., motion) without interruption from its beginning to its end. In such embodiments, it may be immaterial at which time instance the curve starts and how long in time the curve is. Removal of the object from the display area can then determine the curve's end. Furthermore, the drawing direction (i.e. the direction in which the curve is drawn with respect to the time axis) may be immaterial and may thus be drawn forward or backward in time.

The input device may also be provided by or comprise a pointing device such as a mouse, a touchpad, a trackball or any other device that moves the cursor on the display area of a computer and allows the user to input continuous data. In such embodiments, the curve may provided by continuously moving the pointing device and thereby moving the cursor on the display area of, for example, a PC that is used as input device. The curve is preferentially drawn in one go (e.g., motion) without interruption from its beginning to its end, wherein the button of the pointing device (e.g., mouse) is pressed as long as the actual drawing takes place. In some embodiments, it may be immaterial at which time instance the curve starts and how long in time the curve is. The drawing direction may also be forward or backward in time.

In even some embodiments, the input unit can also be provided by or comprise a scanner or scanning device and the curve can be provided as a drawing that is scanned by the scanner or scanning device. In such embodiments, the curve may be permanently drawn (e.g. with a pen on a sheet of paper) which is then placed in the scanner for scanning.

Each profile segment may be assigned that curve value whose time instance lies in the middle of the time interval subset of the respective profile segment. That is, for the duration of the time interval subset, the curve value assigned to the profile segment corresponding to the time interval subset may be kept constant (i.e. "frozen"). When a transition to a consecutive profile segment occurs, a different curve value may apply. In some alternative embodiments, another curve value, for example the curve value whose time instance corresponds to the starting time or the end time of the time interval subset of the respective profile segment, may be assigned to the respective profile segment. Furthermore, in some embodiments, the average of the curve section whose time interval corresponds to the time interval subset of the respective profile segment may be assigned to the respective profile segment. In some embodiments, the curve values that are assigned to the profile segments are rounded, such as according to a resolution (e.g. 0.1 IU) that is suitable and/or beneficial for the design/mechanics of the employed insulin pump. The amplitude/height of a profile segment thereby defines the basal rate delivery/discharge during its time interval subset.

In some embodiments, the provided curve is smoothed by filtering. In such embodiments, the input unit and/or the calculation unit may have a filter unit such as filter that performs moving averaging or another low pass filter.

It should be appreciated that the methods disclosed herein can be implemented with many different types of insulin pumps. In embodiments where the curve that represents the basal rates is provided manually as continuous function of time, the generation of non-physiological basal rate profiles is less likely and a physiological basal rate profile being can be defined as a continuous basal rate profile.

In some embodiments a monitoring unit is provided that may form part of the insulin pump. In other embodiments, the monitoring unit may be separate from the insulin pump. The deviation between curve values which are assigned to adjacent profile segments can be monitored by the monitoring unit for an excess of a pre-defined threshold. A warning can then be generated by the monitoring unit if excess of the pre-defined threshold is detected. The first profile segment in time and the last profile segment in time may also considered as adjacent profile segments. In particular, the first profile segment in time may be considered adjacent last profile segment in time if basal rate delivery according to the basal rate profile shall be repeated in time. The warning can, for example, be in the form of a specific marking of a display of the profile segments on a display area of the input unit, i.e. a specific coloring/hatching of the concerned profile segments. If the pre-defined threshold is exceeded, then the deviation between the curve values assigned to adjacent profile segments is deemed to be physiologically too large. In some embodiments, the pre-defined threshold is defined by the user. In some embodiments, the pre-defined threshold is fixedly set by the manufacturer of the insulin pump. The type of the marking, such as its intensity, distinctness and/or color, can depend on the amount of deviation between curve values assigned to adjacent profile segments in case of an excess of the pre-defined threshold. For example, the warning/marking may have the form of a sliding indication, wherein a color, a gray shade or the like of the profile segments can be modified in a substantially continuous way (e.g. continuously from the color white to the color black) in dependence on the deviation or the amount of the deviation, respectively.

Besides the pre-defined threshold for the deviation between adjacent profile segments, additional or alternative approaches may also be used. For example, a threshold for the slope of the profile or parts of it rather than for the absolute deviation, which is especially useful if the length of the respective subsets (time intervals) of the profile segments is not constant, or an average deviation over a number of consecutive profile segments may be used. Furthermore, the value of the threshold may be different depending on whether heights/associated curve values are increasing or decreasing from one profile segment to the next profile segment.

In some embodiments, an automatic correction of the threshold-exceeding adjacent profile segments is performed by the monitoring unit or the calculation unit, such that at least the amplitude value of one of the adjacent profile segments is drawn closer with regard to the height of the other profile segment. In other embodiments, a proposal for corrected amplitude values/heights of the adjacent profile segments can be calculated and presented to a user for approval.

In some embodiments, the generated basal rate profile with its profile segments may be presented together with the provided curve to a user on a display area of the input device. For presentation purposes, the ability may be given for scrolling the base rate profile (and the curve, if applicable) with respect to the time axis. A reference profile (such as a profile according to Renner, Teupe or the like) may be depicted on the display area to aid the user with the provision of the curve representing the basal rate. The reference profile may thereby serve as exemplary curve. Additionally or alternatively to the reference profile, other information deemed useful may be depicted. For example, a curve of past blood glucose values of a patient/user and/or a curve of deviations of blood glucose values from a reference blood glucose value profile may be shown. This may be provided, for example, in drawing the basal rate curve, i.e. the curve representing the basal rate.

Finally, the generated basal rate profile may optionally be further manipulated, e.g. for the generation of a set of basal rate profiles. For manipulation, the basal rate profile may be multiplied by a specific factor and/or a specific constant may be added or subtracted from the basal rate profile. Another optional manipulation comprises the shifting of the border(s) between adjacent profile segments in time domain. For generation of a second basal rate profile, a basal rate profile generated by the methods disclosed herein may be copied and simultaneously scaled and/or shifted in one processing step (for example, already generated basal rate profile A can be multiplied by the factor 1.2 to generate basal rate profile B). Furthermore, the dynamics of a generated base rate profile may be changed by scaling it with a specific scaling factor and/or shifted in time while keeping its mean value constant (if applicable). For example, the manipulation can be performed by subtracting the mean value of the provided curve, scaling the intermediate curve resulting from the subtraction (which has a mean value of zero) with a specific factor, and adding to this (further) intermediate curve resulting from the scaling of the mean value again. Physiologically caused delays of the insulin taking effect may thereby be compensated. Additionally, fixed boluses for the insulin may be set which can be taken into account when generating the basal rate profile according to the method provided herein.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed:

1. A method for setting a basal rate profile for an insulin pump, wherein the basal rate profile defines a basal rate delivery for a selected time interval and has a pre-defined number of profile segments each of which define the basal rate delivery for a subset of the selected time interval, the method comprising:
    providing a curve representing a basal rate as a continuous function of time as an input for an input unit; and
    generating the basal rate profile from the curve by a the calculation unit by assigning curve values at selected time instances to the pre-defined number of profile segments;
    wherein the respective subset of the selected time interval varies for each profile segment, there is a threshold for the average deviation over a number of consecutive profile segments, and when the threshold is exceeded, a proposal for corrected amplitude of adjacent profile segments is calculated and presented to a user for approval; and wherein the basal rate delivery is repeated in time and a first profile segment in time is considered adjacent to a last profile segment in time;
    providing the curve by continuously moving the object across a display area of a touch screen and drawing the curve backward in time or providing the curve as a pre-drawn curve that has been scanned by a scanner; and
    wherein the user can select either one of the steps of providing the curves.

2. The method of claim 1, wherein the curve is provided by continuously moving the object, across the display area.

3. The method of claim 2, wherein the object comprises a finger.

4. The method of claim 1, wherein the input unit comprises a pointing device for inputting continuous data and that the curve is provided by continuously moving the pointing device.

5. The method of claim 4, wherein the pointing device comprises a mouse.

6. The method of claim 1, wherein the the curve is provided as the pre-drawn curve that has been scanned by the scanner.

7. The method of claim 1, wherein each profile segment is assigned that curve value whose time instance lies in the middle of that time interval subset of that particular profile segment.

8. The method of claim 1, wherein the curve values that are assigned to the profile segments are rounded according to a pre-defined resolution.

9. The method of claim 1, wherein a monitoring unit is provided and a deviation between curve values assigned to the adjacent profile segments is monitored by the monitoring unit for an excess of a pre-defined threshold, and wherein a warning is generated by the monitoring unit if excess of the pre-defined threshold is detected.

10. The method of claim 9, wherein a type of the warning, depends on an amount of deviation.

11. The method of claim 10, wherein the type comprises an intensity and/or a distinctness of the warning; and wherein the warning is a sliding indication wherein profile segments are modified in a substantially continuous way by a continuous change of a color from white to black depending on the amount of deviation.

12. The method of claim 1, wherein a reference profile is depicted on the display area of the input unit.

13. The method of claim 1, wherein the generated basal rate profile is scaled with a specific scaling factor while its mean value is kept constant.

14. The method of claim 1, wherein the provided curve is smoothed by filtering.

15. An apparatus that sets the basal rate profile, wherein the basal rate profile defines the basal rate delivery for the selected time interval and has the pre-defined number of profile segments each of which define the basal rate delivery for the subset of the selected time interval, the apparatus comprising:
    the input unit that receives the input of the curve representing the basal rate as the continuous function of time; and
    the calculation unit that generates the basal rate profile from the curve by assigning curve values at selected time instances to the pre-defined number of profile segments according to the method of claim 1.

16. The apparatus of claim 15, wherein the input unit further comprises the touch screen with the display.

17. The apparatus of claim 15, wherein the input unit further comprises a pointing device that inputs continuous data.

18. The apparatus of claim 17, wherein the pointing device comprises a mouse.

19. The apparatus of claim 15, wherein the input unit further comprises the scanner.

20. The apparatus of claim 15 further comprising a monitoring unit that monitors a deviation between curve values assigned to the adjacent profile segments for an excess of the threshold which is pre-defined and generates a warning if excess of the pre-defined threshold is detected.

* * * * *

UNITED STATES PATENT AND TRADEMARK OFFICE
CERTIFICATE OF CORRECTION

| | |
|---|---|
| PATENT NO. | : 8,684,996 B2 |
| APPLICATION NO. | : 13/038635 |
| DATED | : April 1, 2014 |
| INVENTOR(S) | : Ulrich Haueter et al. |

It is certified that error appears in the above-identified patent and that said Letters Patent is hereby corrected as shown below:

In the Specification,

Col. 2, Lines 59-60,
 "matter defined by the claims. The following detailed desertion of the illustrative embodiments can be understood when" should read
 --matter defined by the claims. The following detailed description of the illustrative embodiments can be understood when--;

Col. 3, Line 9,
 "Methods and an apparatuses are also provided for which" should read
 --Methods and apparatuses are also provided for which--;

Col. 3, Line 41,
 "resulting from the scaling the mean value" should read
 --resulting from scaling the mean value--;

Col. 5, Line 33,
 "such embodiments, the curve may provided by continuously" should read
 --such embodiments, the curve may be provided by continuously--;

Col. 6, Line 22,
 "and the last profile segment in time may also considered as" should read
 --and the last profile segment in time may also be considered as--; and In the Claims, Col. 7, Claim 1, Line 64,
 "generating the basal rate profile from the curve by a the" should read
 --generating the basal rate profile from the curve by a--.

Signed and Sealed this
Seventeenth Day of February, 2015

Michelle K. Lee
*Deputy Director of the United States Patent and Trademark Office*